US00PP16576P3

(12) United States Plant Patent
Redman

(10) Patent No.: US PP16,576 P3
(45) Date of Patent: May 30, 2006

(54) ***CHRYSANTHEMUM* PLANT NAMED 'MEGA TIME IMPROVED'**

(50) Latin Name: *Chrysanthemum morifolium*
Varietal Denomination: Mega Time Improved

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 115 days.

(21) Appl. No.: 10/993,258

(22) Filed: Nov. 18, 2004

(65) Prior Publication Data

US 2005/0114968 P1 May 26, 2005

Related U.S. Application Data

(60) Provisional application No. 60/524,336, filed on Nov. 20, 2003.

(51) Int. Cl.
*A01H 5/00* (2006.01)

(52) U.S. Cl. ..... Plt./297
(58) Field of Classification Search ..... Plt./297
See application file for complete search history.

(56) References Cited

PUBLICATIONS

2000 Ficor catalog, listing the variety 'Mega Time'. See, e.g., pp. 4 and 13.

2001 Ficor catalog, listing the variety 'Mega Time'. See, e.g., pp. 4 and 7.

2002 Ficor catalog, listing the variety 'Mega Time'. See, e.g., pp. 4 and 7.

2003 Ficor catalog, listing the variety 'Mega Time'. See, e.g., pp. 2, 3 and 6.

2002 Van Zanten North America catalog, listing the variety 'Mega Time'. See, e.g., pp. 7 and 8 (photograph).

2003 Royal Van Zanten catalog, listing the variety 'Elgon Light Pink'. See, e.g., pp. 39 (photograph) and 59.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Mega Time Improved,' having a flat capitulum of light pink single flowers with a dark spot in the disc.

1 Drawing Sheet

Latin name of the genus and species: Botanical classification: *Chrysanthemum morifolium.*

Variety denomination: The new *Chrysanthemum* variety denomination is 'Mega Time Improved. '

BACKGROUND OF THE INVENTION

The present invention comprises a new and distinct cultivar of *Chrysanthemum* botanically known as *Chrysanthemum morifolium,* and referred to by the cultivar name 'Mega Time Improved.'

'Mega Time Improved' identified as 20929-0A was discovered as a whole plant natural mutation in a controlled cultivated planting of the variety 'Mega Time,' an unpatented seedling. The new variety 'Mega Time Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Mega Time Improved' is a pot type of *Chrysanthemum* plant variety having a flat capitulum of light pink single flowers with a dark spot in the disc.

Comparison With Parent

Plants of the new *Chrysanthemum* variety 'Mega Time Improved' are similar to the parent variety 'Mega Time' in plant habitat and growth rate. In side-by-side comparisons in Chichester, West Sussex, United Kingdom, under commercial practice, plants of the new *Chrysanthemum* variety 'Mega Time Improved' compared to plants of the parent 'Mega Time' in the following characteristics:

1. The new variety 'Mega Time Improved' produces light pink single flowers whereas the parent 'Mega Time' also produces light pink single flowers.
2. Plants of the new variety 'Mega Time Improved' have similar inflorescence to plants of the parent 'Mega Time.'
3. Plants of the new variety 'Mega Time Improved' have a slower response time than the plants of the parent 'Mega Time.'
4. Plants of the new variety 'Mega Time Improved' have a shorter vigor when compared to the plants of 'Mega Time.'

Comparison with Other Varieties

Plants of the new *Chrysanthemum* variety 'Mega Time Improved' are dissimilar to the variety 'Elgon Light Pink' (United States Plant Patent Pending) in plant habitat and growth rate. However, in side-by-side comparisons in Chichester, West Sussex, United Kingdom, under commercial practice, plants of the new *Chrysanthemum* variety 'Mega Time Improved' differed from plants of the variety 'Elgon Light Pink' in the following characteristics:

1. The new variety 'Mega Time Improved' produces light pink single flowers with a dark spot in the disc whereas the variety 'Elgon Light Pink' produces light pink single flowers.

2. Plants of the new variety 'Mega Time Improved' have larger and taller inflorescence than plants of 'Mega Time Improved.'
3. The new variety 'Mega Time Improved' has a slower response time than the plants of 'Elgon Light Pink.'

BRIEF DESCRIPTION OF ILLUSTRATIONS

Typical specimens of the plant and flowers for the new *Chrysanthemum* variety 'Mega Time Improved' are shown in the accompanying digital photograph. The colors shown are as true as possible within the usual limits of this kind of illustration.

FIG. 1 is a whole plant view of the new variety 'Mega Time Improved' grown in a pot. The plant shown in the illustration is 60 days from the commencement of short days.

DETAILED BOTANICAL DESCRIPTION

The following description of the new *Chrysanthemum* variety 'Mega Time Improved' is of plants grown in a greenhouse in Chichester, West Sussex, United Kingdom in the month of April. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gram per liter. To produce a commercial product the plants may be pinched once with the center bud removed. The typical container size for commercial growth is 1 liter. It has been observed that the shelf life of the new variety is about 28 days with a response time of about 8 weeks. The new variety is suitable for growth in a temperature range of 15° C. to 25° C.

The new variety may be produced as a spray or disbud. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright.
Height (cm): 24 cm.
Width (cm): 35 cm.
Stem:
- *Length* (*cm*).—5.5.
- *Diameter* (*cm*).—0.8.
- *Texture.*—Slightly pubescent.
- *Color.*—137B.

Branching characteristics: Upright and free branching.
Lateral branches:
- *Length* (*cm*).—19.
- *Diameter* (*cm*).—0.8.
- *Texture.*—Slightly pubescent.

Number of breaks from pinch: 6.
Response time: 55 days.
Vigor: Medium.
Shelf life: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type.*—Vegetative Propagation Via Stem Cuttings.
- Time to rooting.—14 days with soil temperatures of 18° C.
- *Rooting habit.*—After 7 days the first roots emerge and form root primordia. In 14 long days a complete root system is developed.

Foliage

Number of leaves per lateral branch: 12.
Compound or single: single.
Arrangement of leaves: Alternate.
- *Shape of leaf.*—5 lobed.
- *Size of leaf.*—Width (cm): 4. Length (cm): 6.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: slightly purbescent. Bottom: pubescent.

Petiole:
- *Color.*—137D.
- *Length* (*cm*).—1.5.
- *Diameter* (*cm*).—0.2.

Venation:
- *Color.*—Upper side: 137C. Under side: 138B.

Color:
- *Mature leaf, upper side.*—137B; under side: 138A.
- *Young leaf, upper side.*—137A; under side: 137D.

Flower

Flower appearance: Matte.
Flower type: Single.
Flower form: Slightly cupped.
Flower shape: Round.
Flowering habit: Cyme.
Number of blossoms per branch: 6.
Typical and observed flowering season: January to December.
Inflorescence form: Cyme.
- *Depth of fully expanded blossoms* (*cm*).—2.
- *Diameter of fully expanded blossoms* (*cm*).—7.

Phyllaries:
- *Number.*—20.
- *Color.*—137C.
- *Length* (*cm*).—0.8.
- *Width* (*cm*).—0.2.
- *Texture/appearance.*—Pubescent.

Peduncle:
- *Length* (*cm*).—12.
- *Diameter* (*cm*).—0.8.

*Angle from stem* (*degrees*).—10.
*Color.*—137C.
*Surface.*—Pubescent.
*Habit.*—Slightly undulating.
*Strength.*—Medium.

Pedicel:
*Length.*—Terminal (cm): 3; lateral (cm): 4.5.
*Diameter* (*cm*).—0.3.
*Color.*—137C.
*Surface.*—Pubescent.
*Habit.*—Slightly undulating.
*Strength.*—Medium.

Ray florets:
*Form/shape.*—Straight.
*Texture/appearance.*—Matte.
*Number per flower.*—25.
*Length* (*cm*).—3.5. Width (cm): 1.
*Apex.*—Rounded.
*Base.*—Tapered.
*Margin.*—Entire.

Disc florets:
*Form/shape.*—Cylindric.
*Texture/appearance.*—Shiny.
*Number per flower.*—120.
*Length* (*cm*).—0.6; Width (cm): 0.1.
*Diameter of disc* (*cm*).—1.3.

Fragrance: None.

Flower bud (at onset of color):
*Length* (*cm*).—1.
*Diameter* (*cm*).—1.
*Form/shape.*—Spherical.

General flower color:
1. *Ray florets, upper side.*—Immature: 75C. Mature: 75D. Older/Fading: 75D.
2. *Ray florets, under side.*—Immature: 65B. Mature: 65C. Older/Fading: 65C.
3. *Disc florets.*—Immature: 152C. Mature: 15C. Older/Fading: 174B.
4. *Bud.*—65B.

Flower progression with age: Flower form does not change but there is a slight color fading with age.

Other distinguishing characteristics: The disc has a dark spot.

Reproductive Organs

Gynoecium present on Ray and/ Disc florets.

Ray florets per individual flower: Pistillate.
*Pistil number.*—25.
*Stigma color.*—154A.
*Stigma shape.*—Forked.
*Style color.*—154B.
*Style length* (*cm*).—0.3.

Disc florets per individual flower: Pistillate.
*Pistil number.*—120.
*Stigma color.*—154A.
*Stigma shape.*—Forked.
*Style color.*—154B.
*Style length* (*cm*).—0.3.

Androecium: None observed.

Fruit and seeds: None.

What is claimed is:

1. A new and distinct variety of *Chrysanthemum* plant, substantially as described and illustrated herein.

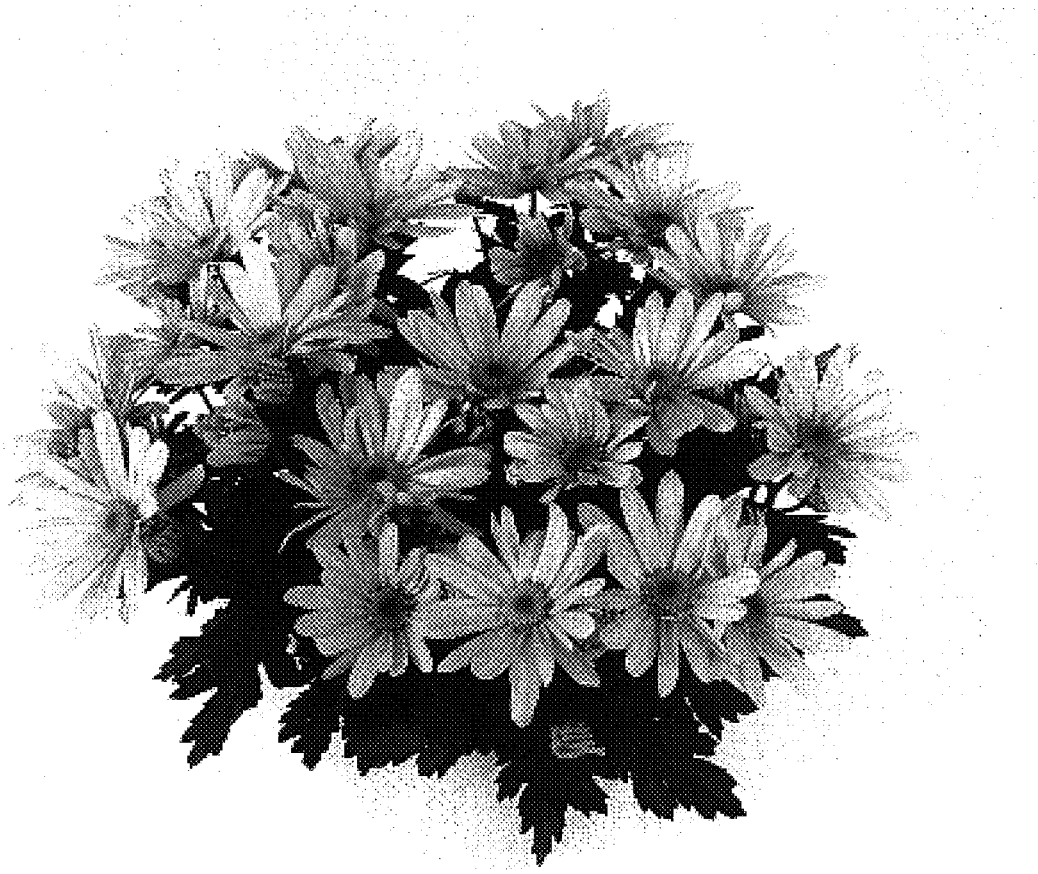

* * * * *